United States Patent [19]

Beach et al.

[11] Patent Number: 4,686,315

[45] Date of Patent: Aug. 11, 1987

[54] OLIGOMERIZATION OF ETHYLENE USING NICKEL YLIDE/ALKYL ALUMINUM ALKOXIDE CATALYST

[75] Inventors: David L. Beach, Kingwood, Tex.; Yury V. Kissin, East Brunswick, N.J.

[73] Assignee: Chevron Research Company, San Francisco, Calif.

[21] Appl. No.: 940,826

[22] Filed: Dec. 12, 1986

[51] Int. Cl.$^4$ .......................... C07C 2/02; C07C 2/36
[52] U.S. Cl. ................................. 585/513; 585/514; 585/515; 585/526; 585/527; 585/531; 502/117
[58] Field of Search .............. 585/513, 512, 514, 515, 585/526, 527, 531; 502/117

[56] References Cited

U.S. PATENT DOCUMENTS

| | | |
|---|---|---|
| 3,505,425 | 4/1970 | Jones et al. ......................... 585/512 |
| 3,558,738 | 1/1971 | Dunn ................................... 585/513 |
| 3,592,870 | 7/1971 | Dunn ................................... 585/513 |
| 4,293,502 | 10/1981 | Beach et al. ........................ 556/20 |
| 4,293,727 | 10/1981 | Beach et al. ........................ 585/526 |
| 4,301,318 | 11/1981 | Beach et al. ........................ 585/526 |
| 4,310,716 | 1/1982 | Beach et al. ........................ 585/526 |
| 4,377,528 | 3/1983 | Beach et al. ........................ 585/526 |
| 4,377,529 | 3/1983 | Beach et al. ........................ 556/20 |
| 4,382,153 | 5/1983 | Beach et al. ........................ 585/526 |
| 4,476,341 | 10/1984 | Mathys ................................ 585/512 |

*Primary Examiner*—Asok Pal
*Attorney, Agent, or Firm*—S. R. La Paglia; T. G. DeJonghe

[57] ABSTRACT

A process for oligomerizing ethylene using a bicomponent catalyst comprising a nickel ylide substituted with a sulfonato group and an alkyl aluminum alkoxide.

31 Claims, No Drawings

OLIGOMERIZATION OF ETHYLENE USING NICKEL YLIDE/ALKYL ALUMINUM ALKOXIDE CATALYST

CROSS-REFERENCE TO RELATED PATENTS AND APPLICATIONS

Reference is made to the following U.S. Patents and application in which Applicant D. L. Beach is a co-inventor:

U.S. Pat. No. 4,293,502, Nickel Ylides, issued Oct. 6, 1981;

U.S. Pat. No. 4,293,727, Process for Oligomerization of Ethylene, issued Oct. 6, 1981;

U.S. Pat. No. 4,310,716, Process for Oligomerization of Ethylene in Methanol, issued Jan. 12, 1982;

U.S. Pat. No. 4,377,528, Group VA Salts and Process for Preparing Same, issued Mar. 22, 1983;

U.S. Pat. No. 4,377,529, Sulfonated Group VA Ylides and Process for Preparing Same, issued Mar. 22, 1983;

U.S. Pat. No. 4,382,153, Process for Oliogomerization of Ethylene in Methanol, issued May 3, 1983; and U.S. Pat. No. 4,529,554, Process for the Preparation of Nickel Ylides Conatining Ylide Ligands with a Sulfonated Group V Component, issued July 16, 1985.

U.S. Ser. No. 900,204 filed Aug. 25, 1986, Oliogomerization of Ethylene in Methanol and Water.

FIELD OF THE INVENTION

The present invention relates to the use of nickel ylides with alkyl aluminum alkoxide to oliogomerize ethylene.

DESCRIPTION OF THE PRIOR ART

It is well known in the art to use a variety of catalysts to oligomerize ethylene to higher molecular weight olefins. The term "oligomerize" has been employed, and is employed herein to described the conversion of lower olefins such as ethylene to olefinic products of higher molecular weight, e.g., to dimer, trimer, tetramer and the like. The reaction rate and product distribution obtained are highly dependent on the exact catalyst composition and the reaction conditions employed. Two such general classes of catalysts are the "Ziegler" types consisting of aluminum trialkyls or dialkylaluminum alkoxides and the "Ziegler-Natta" types consisting of aluminum trialkyls or alkyl aluminum chlorides and titanium halides. Major disadvantages of aluminum trialkyl or dialkylaluminum alkoxide catalysts are their highly reaction and pyrophoric nature and the fact that they must be used at relatively high temperatures, e.g., 200° C. to 275° C. and pressures, e.g., 2000 to 4000 psig. Although much milder reaction conditions are used when the aluminum alkyls are used in conjunction with titanium halides, product quality and ease of catalyst separation from products of both of these prior art types of catalysts are not as high as desired.

An article by W. Keim, F. H. Kowaldt, R. Goddard and C. Kruger entitled "Novel Coordination of (Benzoylmethylene) triphenylphosphorane in a Nickel Oligomerization Catalyst", in Angew. Chem. Int. Ed. Engl. (1978) No. 6, page 466, discloses that a nickel ylide having the structure:

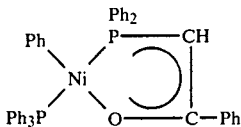

converts ethylene into alpha olefins or polyethylene.

The earlier cases of co-inventor Beach referenced above are directed to use of Nickel ylides as catalysts for ethylene oligomerization. These catalysts are particularly suitable for ethylene oligomerization in polar solvents such as halogenated hydrocarbons, alcohols, ketones, ethers, etc. These catalysts are also moderately active for ethylene oligomerization in nonpolar solvents such as aromatic solvents. The present application is directed to the use of bicomponent catalytic systems for ethylene digomerization which include nickel ylides and alkyl aluminum alkoxides or mixtures of different alkyl aluminum alkoxides.

Alkyl aluminum and alkyl aluminum alkoxide compounds and their preparation are described in Kirk Othmer, 3rd Edition, Volume 16, p. 565-572, which disclosure is incorporated herein by reference, particularly as related to preparation of alkyl aluminum and alkyl aluminum alkoxide.

U.S. Pat. No. 3,424,815 to Cannell et al. disclose the use of catalyst consisting of (a) nickel helate wherein the helate liqand and is a halogenated B-dicarbonylic monoenalate and (b) a halide free alkyl aluminum alkoxide.

SUMMARY OF THE INVENTION

According to the present invention, a process is provided for oligomerizing ethylene to normal alpha olefins, that is, straight chain alpha olefins, which process comprises reacting ethylene under oligomerization conditions in contact with a bicomponent catalyst comprising (a) a nickel ylide defined by the following formula:

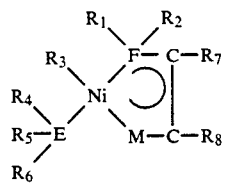

wherein $R_1$, $R_2$, $R_3$, $R_4$, $R_5$, $R_6$, $R_7$ and $R_8$ are either alike or different members selected from the group consisting of hydrogen, alkyl radicals having from about 1 to about 24 carbon atoms, aryl radicals having from about 6 to about 20 carbon atoms, alkenyl radicals having from about 2 to about 30 carbon atoms, cycloalkyl radicals having from about 3 to about 40 carbon atoms, aralkyl and alkaryl radicals having from about 6 to about 40 carbon atoms, halogen radicals, hydroxyl, alkoxy and aryloxy groups, and hydrocarbyl groups carrying halogen, hydroxyl, alkoxy or aryloxy groups, provided that at least one of each $R_1$ to $R_8$ radicals is a sulfonato group or an alkyl, aryl, alkenyl, cycloalkyl, aralkyl or alkaryl carrying a sulfonator group, M is sulfur or oxygen, E is phosphorus, arsenic, antimony or nitrogen and F is phosphorus, arsenic or antimony; and (b) an aluminum compound or mixtures of aluminum compounds defined by the formula $R^1_{3-n}AL(OR^2)_n$ where $R^1$ is an alkyl group of 1 to 10 carbon atoms, $R^2$ is an aliphatic group of 1 to 12 carbon atoms, and n is 1, 2, or 3;

to obtain a reaction product containing normal alpha olefins and recovering the normal alpha olefins from the reaction product.

As stated earlier, each of the components of the bicomponent catalytic systems of the present invention represent catalysts for ethylene oligomerization by themselves. We have unexpectedly found, however, that when these chemical compounds are combined, they produce new bicomponent catalysts which are significantly more active in ethylene oligomerization than each of their components, when used under identical conditions. In contrast, we have also found that other bicomponent systems including nickel ylides and certain related compounds, such as triethyl aluminum, are not active in ethylene oligomerization, and that compositions comprising nickel ylides and alkyl aluminum chlorides are not effective for oligomerizing ethylene to C6 and higher olefins but are effective for ethylene dimerization to butene mixtures, as described earlier by us in *Journal of Polymer Science, Polymer Chemistry Edition*, Volume 22, pp. 3033–3042, 1984.

The alkyl aluminum alkoxide component of the catalyst used in the process of the present invention has, as previously stated, the formula $(R^1)_{3-n}Al(OR^2)_n$. Preferably $R^1$ is a 1 to 6 carbon atom alkyl group; more preferably 1 to 4 carbon atoms; still more preferably methyl, ethyl, n-propyl, n-butyl, or isobutyl; and most preferably $R^1$ is ethyl. Preferably $R_2$ is an aliphatic hydrocarbyl group having 1 to 6 carbon atoms; more preferably 1 to 4 carbon atoms; still more preferably methyl, ethyl, n-propyl, n-butyl, or isobutyl; and most preferably ethyl. Preferably n is 1 or 2, most preferably 1.

The alkyl aluminum alkoxide component of the catalyst may be prepared in accordance with known techniques or the alkoxide may be purchased. If the alkyl aluminum alkoxide component (i.e., $R^1_{3-n}Al(OR^2)_n$) is prepared starting with trialykl aluminum, the amount of alkoxide can be controlled by reacting varying amounts of alcohol ($R^2OH$) with the alkyl aluminum. Thus the use of one stoichiometric molar amount of alkoxide per mole of trialkyl aluminum will produce $R^1_2AlOR^2$; the use of two moles per mole of trialkyl aluminum will produce $R^1_1Al(OR^2)2$; and the use of three moles alcohol will produce $Al(OR^2)_3$. The alkyl aluminum alkoxide can be prepared in a separate synthesis. Alternatively, according to a preferred embodiment of our process, we have found that the alkyl aluminum alkoxide is advantageously produced immediately prior to use by reacting an appropriate aluminum alkyl compound and alcohol in the reaction solvent which is subsequently used in the oligomerization reaction. We have found that this latter method of in situ alkyl aluminum alkoxide preparation is a particularly effective method of preparing the catalyst.

Preferred ratio for the nickel ylide component to alkyl aluminum alkoxide component of the bicomponent catalysts used in the process of the present invention are from 10:1 to 1:1000; more preferably from 1:1 to 1:500; and still more preferably from 1:50 to 1:400. Thus one example of a particularly preferred ratio is 1 mole of the nickel ylide component to 200 moles of the alkyl aluminum alkoxide component.

We have found that the process of the present invention is preferably carried out in nonpolar hydrocarbon solvents as opposed to polar solvents or use of halogenated hydrocarbons which are preferred in the case of monocomponent nickel ylide catalysts.

The solvent used to carry the catalyst may be any organic solvent in which the nickel ylide and alkyl aluminum alkoxide are soluble and which is substantially inert to reaction with the catalyst components. Example solvents are aliphatic and aromatic hydrocarbons, preferably having from 4 to 10 carbon atoms. More preferred solvents have 6 to 9 carbon atoms; still more preferred are benzene, toluene, ortho, meta and paraxylene, 1,3,5-trimethylbenzene, and heptane; and most preferred is toluene.

In oligomerizing ethylene with the bicomponent catalysts defined herein, the nickel ylide and alkyl aluminum alkoxide are preferably dissolved in an appropriate solvent, for example toluene, such that the concentration of the nickel ylide therein will be in the range of about 0.0001 to about 10 moles per liter of solvent, preferably from 0.001 to about 1.0 mole per liter of solvent and the alkyl aluminum alkoxide is present in a ratio amount to the nickel ylide, as described above. In certain modifications of the process, a portion of the oligomer product can suitably serve as at least a part of the reactor diluent. Ethylene is then added to the reaction zone and pressure is maintained therein within the range of about 10 to 5000 psig, preferably about 50 to 1200 psig. The nickel ylide concentration in the solution will be preferably in the range of about 0.001 to about 20 moles per liter, more preferably about 0.01 to about 10 moles per liter. The temperature is maintained between about $-20°$ to about 200° C., preferably about 20° to about 150° C., while the reaction time can be from about 1 minute to about 72 hours, but preferably from about 10 minutes to about 8 hours. During the reaction, the reaction mixture is preferably stirred.

Solvent and catalyst can be removed from the reaction product by any convenient means, for example, distillation, extraction or absorption, after which the olefinic oligomers can also be recovered by distillation or extraction.

Although various methods may be used for reaction product separation one possible sequence of steps is as follows: First the pressure is reduced on the reaction zone effluent to assist in removing ethylene and the ethylene is recycled to the reaction zone. The liquid from this first step is passed to a gas-liquid separator where the pressure is reduced further and additional ethylene is removed for recycle or venting from the system. The liquid from this further pressure reduction step can be contacted with water to separate the catalyst from the solvent and product oligomers. The alkoxide will be hydrolyzed to aluminum hydroxide and the catalyst/aqueous phase may be discarded or further processed for recovering of catalyst components. The organic phase from the hydrolysis step contains the solvent and product oligomers. These two remaining components may be separated by fractionation to obtain solvent for recycle to the reaction zone and the product oligomers.

The term "oligomerizing ethylene" is used herein to means conversion of ethylene to oligomers which are at least 60 weight percent C6 and higher oligomers. The product oligomers will typically be mostly in the C6 to C30 range, but may range from C4 to as high as C100. Fractionation such as by distillation can be used to separate the product oligomers into various normal alpha olefin cuts or fractions.

The nickel-containing components of the catalysts used in the process of the present invention are the nickel ylides as set forth in the prior Beach et al. patents listed above under Cross References, particularly including U.S. Pat. No. 4,310,716; U.S. Pat. No. 4,293,502; and U.S. Pat. No 4,293,727, the disclosures of which patents are incorporated herein by reference. The same nickel-containing compounds which are preferred in those cited patents are preferred herein. Likewise, preferred catalyst preparation procedures including methods of including a sulfonate group in the catalyst, and preferred reaction conditions such as temperatures, pressures, catalyst concentration and residence time, are as described in the cited patents, especially U.S. Pat. No. 4,310,716, U.S. Pat. No. 4,293,502 and U.S. Pat. No. 4,293,727. However, preferred solvents for use in the oligomerization reaction zone are not the methanol and/or water but rather are aliphatic or aromatic hydrocarbons in which both the nickel ylide and alkyl aluminum alkoxide components of the catalyst are soluble.

EXAMPLES

Ethylene oligomerization reactions were carried out using a sulfonated nickel ylide catalyst and using bicomponent catalysts comprising a sulfonated nickel ylide and alkyl aluminum alkoxide components. The sulfonated nickel ylide catalyst used was Compound 9 of U.S. Pat. No. 4,310,716, which has the following structure:

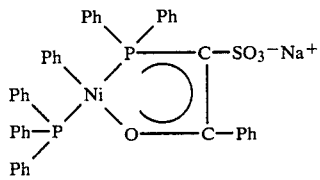

The sulfonated nickel ylide catalyst was prepared in accordance with the Example III preparation of U.S. Pat. No. 4,310,716.

Results for experiments using no alkyl aluminum alkoxide and using the mono-alkoxide, dialkoxide and trialkoxide are set forth in Table I below.

Alkyl aluminum compounds were purchased from Alpha Products Company. Alkylaluminum alkoxides were obtained from the corresponding aluminum alkyls by reaction with appropriate amounts of alcohols in 15% n-heptane solution at 20° C. immediately prior to use. All handling steps involving the sulfonated nickel ylide and alkyl aluminum alkoxide were carried out in a glove box containing a pre-purified argon atmosphere. Ethylene oligomerization reactions were carried out in apparatus used for ethylene polymerization with various Ziegler-Natta catalysts and described earlier by us in J. Appl. Polym. Sci., volume 29, page 1171, 1984. It included an Autoclave Engineers 0.5-L autoclave with a Magnedrive stirrer. Purified ethylene (dried over molecular sieves, deoxygenated over a reduced copper catalyst at 100° C., and finally dried by molecular sieves) was fed at constant pressure into the autoclave from a high pressure stainless steel cylinder reservoir.

Ethylene pressure decrease from the reservoir during the course of oligomerization was measured with a gauge and was used for analysis of reaction kinetics.

Before every experiment, the autoclave was kept under vacuum at 100° C. for 1–1.5 h and, after cooling, was filled with a solvent (usually 200 ml of toluene, previously dried over molecular sieves, metallic sodium, and $Al(C_2H_5)_3$ and distilled under argon), containing the organoaluminum component of the bicomponent catalyst. The mixture was heated in the autoclave to the desired reaction temperature under ethylene pressure, after which 10 ml of a solution of the second catalyst component, the sulfonated nickel ylide compound in toluene, was added to the system, and the ethylene pressure was raised to the desired reaction pressure. The reaction proceeded at constant pressure for a period of 1–2 h and then was stopped by interruption of ethylene feed to the reactor with subsequent cooling.

Reaction products, ethylene oligomers dissolved in toluene, were analyzed by gas chromatography using a programmable variable temperature Hewlett-Packard 5880A Gas Chromatograph.

Activities of various bicomponent catalysts containing various organoaluminum compounds and sulfonated nickel ylide in ethylene oligomerization were evaluated in toluene solution at 30°–120° C. and ethylene pressure 6.6–14.6 atm. A combination of $AlEt_3$ and sulfonated nickel ylide (ca. 20:1) was found to be completely inactive in oligomerization. In contrast, we found that alkyl aluminum alkoxides (for example, prepared in reactions between $AlEt_3$ or $Ali$-$Bu_3$ [aluminum triisobutyl] and appropriate amounts of alcohols in toluene solution at 20° C.) produce, in combination with the sulfonated nickel ylide component, highly active catalysts for ethylene oligomerization to mixtures containing predominantly linear 1-olefins. The product produced was primarily $C_4$ to $C_{20}$ olefins.

Table I shows conditions of oligomerization and catalyst productivities for various aluminum ethoxides. All three ethoxides are approximately equally active and produce similar oligomer mixtures. Comparison with data reported in Beach et al. U.S. Pat. No. 2,932,727 and U.S. Pat. No. 4,310,716 on productivity of pure sulfonated nickel ylide under similar conditions (50°–120° C., reaction pressure 14.6 atm.) shows that the bicomponent catalysts comprising of sulfonated nickel ylide and aluminum ethoxides have productivity of the catalyst 20–25 times higher at 50° C. (see Table I) and ca. 150 times higher at 120° C. compared to the monocomponent sulfonated nickel ylide catalyst. Aluminum alkoxides, when used alone under oligomerization reaction conditions, are unreactive in ethylene oligomerization. We also found that changing the solvent to 1,2-dichloroethane or carbon tetrachloride results in a complete deactivation of the bicomponent catalysts systems.

Combinations of sulfonated nickel ylide and $Ali$-$Bu_2$-$(Oi$-$Bu)$ or $Ali$-$Bu(Oi$-$Bu)_2$ (produced in reaction between $Ali$-$Bu$ and $i$-$BuOH$) were also found to produce active catalysts for ethylene oligomerization. Their productivities are ca. 60–70% of those of the Al ethoxide-based systems.

TABLE I

|  | Sulfonated Nickel Ylide Only[a] | Sulfonated Nickel Ylide + $AlEt_2OEt$ | Sulfonated Nickel Ylide + $AlEt(OEt)_2$ | Sulfonated Nickel Ylide + $Al(OEt)_3$ |
|---|---|---|---|---|
| Ni ylide, g | 0.0025 | 0.0025 | 0.0025 | 0.0025 |
| Al:Ni, molar | 0 | 200 | 200 | 200 |
| Temp., °C. | 50 | 50 | 50 | 50 |
| Reaction | 14.6 | 14.6 | 14.6 | 14.6 |

TABLE I-continued

|  | Sulfonated Nickel Ylide Only[a] | Sulfonated Nickel Ylide + AlEt$_2$OEt | Sulfonated Nickel Ylide + AlEt(OEt)$_2$ | Sulfonated Nickel Ylide + Al(OEt)$_3$ |
|---|---|---|---|---|
| Pressure, atm. |  |  |  |  |
| Reaction time, min. | 120 | 180 | 180 | 185 |
| Yield of oligomers, g/g SUNY | 700 | 18,000 | 16,700 | 14,800 |
| Yield of oligomers, mol/mol SUNY | $2 \times 10^4$ | $5.2 \times 10^5$ | $4.8 \times 10^5$ | $4.2 \times 10^5$ |

[a]Data from U.S. Pat. No. 4,293,727

What is claimed is:

1. A process for oligomerizing ethylene to normal alpha olefins which comprises reacting ethylene under oligomerization conditions in contact with a bicomponent catalyst comprising:

(a) a nickel ylide defined by the following formula:

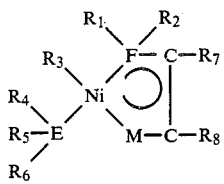

wherein $R_1$, $R_2$, $R_3$, $R_4$, $R_5$, $R_6$, $R_7$ and $R_8$ are either alike or different members selected from the group consisting of hydrogen, alkyl radicals having from about 1 to about 24 carbon atoms, aryl radicals having from about 6 to about 20 carbon atoms, alkenyl radicals having from about 2 to about 30 carbon atoms, cycloalkyl radicals having from about 3 to about 40 carbon atoms, aralkyl and alkaryl radicals having from about 6 to about 40 carbon atoms, halogen radicals, hydroxyl, alkoxy and aryloxy groups, and hydrocarbyl groups carrying halogen, hydroxyl, alkoxy or aryloxy groups, provided that at least one of each $R_1$ to $R_8$ radicals is a sulfonato group or an alkyl, aryl, alkenyl, cycloalkyl, aralkyl or alkaryl carrying a sulfonato group, M is sulfur or oxygen, E is phosphorus, arsenic, antimony or nitrogen and F is phosphorus, arsenic or antimony; and (b) an alkyl aluminum alkoxide or mixtures of alkylaluminum alkoxides defined by the following formula:

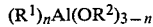

(R$^1$)$_n$Al(OR$^2$)$_{3-n}$ where R$^1$ is an alkyl of 1 to 10 carbon atoms, R$^2$ is an aliphatic group of 1 to 12 carbon atoms, and n is 1, 2 or 3;

to obtain a reaction product containing normal alpha olefins.

2. A process as defined in claim 1 wherein the oligomerizing is carried out in a solvent which is an aliphatic or aromatic hydrocarbon having from 4 to 10 carbon atoms.

3. A process a defined in claim 2 wherein the solvent is a hydrocarbon having from 6 to 9 carbon atoms.

4. A process a defined in claim 1 wherein the sulfonato group is in $R_4$, $R_5$ and/or $R_6$ and at least one of $R_4$, $R_5$ and $R_6$ is aryl.

5. A process as defined in claim 1 wherein the sulfonato group is in $R_1$, $R_2$ and or $R_3$.

6. A process as defined in claim 1 wherein $R_7$ comprises a sulfonato group.

7. A process as defined in claim 1 wherein E and F are both phosphorus and M is oxygen.

8. A process as defined in claim 4 wherein E and F are both phosphorus and M is oxygen.

9. A process as defined in claim 5 wherein E and F are both phosphorus and M is oxygen.

10. A process as defined in claim 6 wherein E and F are both phosphorus and M is oxygen.

11. A process as defined in claim 8 wherein each of $R_4$, $R_5$, and $R_6$ is phenyl, one of which is substituted with a sulfonator group.

12. A process as defined in claim 11 wherein each of $R_1$, $R_2$, $R_3$ and $R_8$ is phenyl and $R_7$ is hydrogen.

13. A process as defined in claim 9 wherein each of $R_1$, $R_2$ and $R_3$ is phenyl, one of which is substituted with a sulfonato group.

14. A process as defined in claim 13 wherein each of $R_4$, $R_5$, $R_6$ and $R_8$ is phenyl and $R_7$ is hydrogen.

15. A process as defined in claim 10 wherein each of $R_1$, $R_2$, $R_3$, $R_4$, $R_5$, $R_6$ and $R_8$ is phenyl and $R_7$ is a sulfonato group.

16. A process as defined in claim 15 wherein said ylide is in the form of its sodium salt.

17. A process as defined in claim 1 wherein R$^1$ contains 1 to 6 carbon atoms and R$^2$ contains 1 to 6 carbon atoms.

18. A process as defined in claim 17 wherein R$^1$ and R$^2$ independently are methyl, ethyl, n-propyl, n-butyl or iso-butyl.

19. A process as defined in claim 18 wherein R$^1$ and R$^2$ are ethyl and n is 1 or 2.

20. A process as defined in claim 19 wherein n is 1.

21. A process as defined in claim 1 wherein the alkyl aluminum alkoxide is produced immediately prior to the oligomerization reaction by steps comprising contacting an aluminum alkyl and alcohol in a solvent medium which is subsequently used in the oligomerization reaction.

22. A process as defined in claim 17 or 20 wherein the ratio of the nickel ylide to the alkyl aluminum alkoxide is from 1:1 to 1:500.

23. A process as defined in claim 1 wherein the ethylene and the nickel ylide and (R$^1$)$_n$Al(OR$^2$)$_{3-n}$ are contacted at a temperature of from about $-20°$ C. to about 200° C. for about 1 minute to 72 hours.

24. A process as defined in claim 1 wherein the ethylene and the nickel ylide (R$^1$)$_n$Al(OR$^2$)$_{3-n}$ are contacted at a temperature of from about 20° C. to about 150° C.

25. A process as defined in claim 17 or 20 wherein the ethylene and the nickel ylide (R$^1$)$_n$Al(OR$^2$)$_{3-n}$ are contacted at a temperature of from about $-20°$ C. to about 200° C. for about 1 minute to 72 hours.

26. A process as defined in claim 17 or 20 wherein the ethylene and the nickel ylide (R$^1$)$_n$Al(OR$^2$)$_{3-n}$ are contacted at a temperature of from about 20° C. to about 150° C.

27. A process as defined in claim 1 wherein the oligomerizing reaction is carried out at a pressure in the range of about 10 to about 5000 psig.

28. A process as defined in claim 27 wherein the pressure is 50 to 1200 psig.

29. A process as defined in claim 17 or 20 wherein the oligomerizing reaction is carried out at a pressure in the range of about 50 to about 1200 psig.

30. A process as defined in claim 20 wherein the oligomerizing is carried out in the presence of benzene, toluene, ortho-xylene, metal-xylene, para-xylene, 1,3,5-trimethyl benzene, or heptane solvent.

31. A process as defined in claim 30 wherein the solvent is toluene.

* * * * *